(12) United States Patent
Abels et al.

(10) Patent No.: US 6,607,383 B2
(45) Date of Patent: Aug. 19, 2003

(54) ORTHODONTIC BRACKET

(75) Inventors: Norbert Abels, 66424 Talstrasse 7, Homburg (DE); Claus H. Backes, St. Wendeler Strasse 45, 66113 Saarbrücken (DE)

(73) Assignees: Norbert Abels (DE); Claus H. Backes (DE)

( * ) Notice: Subject to any disclaimer, the term of this patent is extended or adjusted under 35 U.S.C. 154(b) by 0 days.

(21) Appl. No.: 09/784,525

(22) Filed: Feb. 15, 2001

(65) Prior Publication Data

US 2002/0025500 A1 Feb. 28, 2002

(30) Foreign Application Priority Data

Mar. 10, 2000 (DE) .......................... 100 11 596

(51) Int. Cl.$^7$ .................................................. A61C 3/00
(52) U.S. Cl. ....................................................... 433/11
(58) Field of Search ................................ 433/10, 11, 8, 433/9

(56) References Cited

U.S. PATENT DOCUMENTS

| | | |
|---|---|---|
| 2,011,575 A | 8/1935 | Ford |
| 3,128,552 A | 4/1964 | Broussard |
| 3,218,713 A | 11/1965 | Wallshein |
| 3,724,074 A | 4/1973 | Wallshein |
| 3,748,740 A | 7/1973 | Wildman |
| 3,854,207 A | 12/1974 | Wildman |
| 4,077,126 A | 3/1978 | Pletcher |
| 4,103,423 A | 8/1978 | Kessel |
| 4,144,642 A | 3/1979 | Wallshein |
| 4,171,568 A | 10/1979 | Föorster |
| 4,180,912 A | 1/1980 | Kesling |
| 4,279,593 A | 7/1981 | Röhlcke |
| 4,371,337 A | 2/1983 | Pletcher |
| 4,419,078 A | 12/1983 | Pletcher |
| 4,492,573 A | 1/1985 | Hanson |
| 4,527,975 A | 7/1985 | Ghafari et al. |
| 4,559,012 A | 12/1985 | Pletcher |
| 4,559,013 A | 12/1985 | Amstutz et al. |
| 4,597,739 A | 7/1986 | Rosenberg |
| 4,614,497 A | 9/1986 | Kurz |
| 4,634,662 A | 1/1987 | Rosenberg |
| 4,655,708 A | 4/1987 | Fujita |
| 4,687,441 A | 8/1987 | Klepacki |
| 4,698,017 A | 10/1987 | Hanson |
| 4,712,999 A * | 12/1987 | Rosenberg .............. 433/8 |
| 4,786,252 A | 11/1988 | Fujita |
| 4,846,681 A | 7/1989 | Mourany et al. |

(List continued on next page.)

FOREIGN PATENT DOCUMENTS

| | | |
|---|---|---|
| DE | 1 184 451 | 12/1964 |
| DE | 23 57 573 | 5/1975 |
| DE | 91 12 872.2 | 3/1992 |
| DE | 296 08 349 U1 | 11/1996 |
| EP | 0 714 639 A3 | 6/1996 |
| EP | 0 714 639 A2 | 6/1996 |
| WO | WO 94/00072 | 1/1994 |
| WO | WO 00/33760 | 6/2000 |
| WO | WO 00/76419 | 12/2000 |

OTHER PUBLICATIONS

Konstruieren mit sunststoffen, Gunter Erhard, Carl Hanser Verlag München Wien, pp. 314–329, 1999.

*Primary Examiner*—John J. Wilson
(74) *Attorney, Agent, or Firm*—Workman, Nydegger & Seeley

(57) ABSTRACT

An orthodontic bracket has a base with a slot configured to receive an archwire. A cover is hingedly fastened to the base and is operable between an open and closed position. The cover covers at least a portion of the slot on the base when in the closed position. A spring element extends between the base and the cover.

24 Claims, 2 Drawing Sheets

U.S. PATENT DOCUMENTS

| | | |
|---|---|---|
| 4,850,865 A | 7/1989 | Napolitano |
| 4,859,179 A | 8/1989 | Kesling .......................... 433/8 |
| 4,913,654 A | 4/1990 | Morgan et al. |
| 5,037,296 A | 8/1991 | Karwoski |
| 5,062,794 A | 11/1991 | Miura |
| 5,078,596 A | 1/1992 | Carberry et al. |
| 5,094,614 A | 3/1992 | Wildman |
| 5,125,832 A | 6/1992 | Kesling |
| 5,160,260 A | 11/1992 | Chang |
| 5,161,969 A | 11/1992 | Pospisil et al. |
| 5,174,754 A | 12/1992 | Meritt |
| 5,224,858 A | 7/1993 | Hanson |
| 5,275,557 A | 1/1994 | Damon |
| 5,322,435 A | 6/1994 | Pletcher |
| 5,344,315 A | 9/1994 | Hanson |
| 5,380,197 A | 1/1995 | Hanson |
| 5,456,599 A | 10/1995 | Hanson |
| 5,470,228 A | 11/1995 | Franseen et al. |
| 5,474,445 A | 12/1995 | Voudouris |
| 5,474,446 A | 12/1995 | Wildman et al. |
| 5,556,276 A | 9/1996 | Roman et al. |
| 5,562,444 A | 10/1996 | Heiser et al. |
| 5,586,882 A | 12/1996 | Hanson |
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,738,513 A | 4/1998 | Hermann |
| 5,813,852 A * | 9/1998 | Kawaguchi .................... 433/8 |
| 5,857,849 A * | 1/1999 | Kurz .......................... 433/10 |
| 5,863,199 A | 1/1999 | Wildman |
| 5,885,074 A | 3/1999 | Hanson |
| 5,906,486 A | 5/1999 | Hanson |
| 5,964,589 A | 10/1999 | Musich |
| 6,017,118 A | 1/2000 | Gasvoda et al. |
| 6,042,373 A | 3/2000 | Hermann |
| 6,042,374 A | 3/2000 | Farzin-Nia et al. |
| 6,071,119 A | 6/2000 | Christoff et al. |
| 6,220,857 B1 * | 4/2001 | Abels ........................... 433/8 |

* cited by examiner

ORTHODONTIC BRACKET

BACKGROUND OF THE INVENTION

1. The Field of the Invention

The present invention relates to orthodontic brackets.

2. The Relevant Technology

Orthodontic brackets are secured to a patient's teeth for use in selectively straightening the patient's teeth. One type of orthodontic bracket known in the art includes a base having a slot formed thereon. The slot is configured to receive an archwire that extends between different teeth. A separate cover plate is removably attached to the base for use in securing the archwire to the base. One example of the above orthodontic bracket is disclosed in U.S. Pat. No. 4,712,999.

BRIEF SUMMARY OF THE INVENTION

One object of the present invention is to develop an orthodontic bracket of the kind known in the prior art that is low-cost, simple to manufacture, and compact in construction.

The above and other objects of the present invention are satisfied by the features of the present invention as claimed herein and in particular by an inventive orthodontic bracket having a cover and base that are integrally connected together as a single piece. The inventive orthodontic bracket is low-cost and simple to manufacture. This is due in part to the fact that the orthodontic bracket comprises only one single component which does not have to be assembled. In addition, in one embodiment the inventive orthodontic bracket is made from only one single material, preferably plastic. Furthermore, the cover is integrally formed with the base so as to prevent unwanted separation.

Advantageous embodiments are described in the description, the dependent claims and the figures.

In accordance with a first embodiment, a hinge between the base and the cover can be formed by a reduction in the material cross-sections in the hinge region. The orthodontic bracket can be formed in a compact manner by the use of such hinges, which are also known as integral hinges or living hinges.

As an alternative to the integral one piece embodiment of the orthodontic bracket, the cover and the base can be connected to one another via a pluggable connection. This connection permits separation of the cover and the base without tools. The cover can, for example, be connected to the base via a grooved and tongued connection, for example in a dovetail form. It is possible in this way to put the cover onto the base via the pluggable connection, with the groove and tongue being formed so that a force fit is ensured with full insertion.

This last-mentioned embodiment has the advantage that a subsequent fastening of the cover to the base is possible. This can be advantageous for certain positions of the teeth in tight space conditions. It is also possible with this embodiment to remove the cover from the base in a simple manner and, where required, to replace it with a further cover which is merely placed onto the base. Such a procedure is advantageous when it is not or is no longer possible to pivot the cover around the base due to tight space conditions.

In accordance with a further advantageous embodiment, the orthodontic bracket includes a spring element which supports the closing and opening movement of the cover. This ensures that the cover is held in the open position by the spring element so that the opened cover does not hinder the insertion of the archwire. In one embodiment, the spring element is connected to the base and the cover via hinges. The hinges are preferably formed by a reduction of the material cross-sections in the hinge region. The resulting orthodontic bracket has a compact configuration despite the provision of the spring element. Low-cost manufacturing is ensured by the possibility of the bracket being made in one piece, for example, as an injection molded plastic part.

It is particularly advantageous if the spring element is fully integrated in the cover so that the bracket does not have any protruding parts or edges when in the closed state. The comfort in wear is fairly significantly increased in this way since no edges are present which could have an irritating effect for the patient in the mouth region.

In accordance with a further embodiment of the invention, the cover can have a recess which is open to the outside, but closed to the inside, and in which the spring element is completely received in the closed state of the cover. One advantage of this embodiment is that the spring element is completely integrated in the cover with respect to its outside so that a pleasant manner of wear results for the patient.

At the same time, however, the cover is completely closed in the region of the spring element. As a result, no remnants of food or the like can penetrate the inside of the cover.

In accordance with a further advantageous embodiment of the present invention, a reinforcement insert is provided on the base in the region of the slot. The reinforcement insert can be worked into the basic material of the bracket in the manufacturing process. This ensures that the forces acting in the region of the archwire are transferred without loss to the base and thus the tooth to be corrected. At the same time, the manufacturing costs are also reduced in this case since the bracket can be made of plastic in total and only the reinforcement part is made of a hard material, for example, metal.

The bracket in accordance with the invention is preferably formed in a self-ligating manner, i.e., the archwire is clamped between the cover and the base. It can be advantageous for this purpose for a plurality of locking recesses to be provided on the cover or the base in order to close the cover at different opening widths. Archwires having different cross-section sizes can be inserted into the slot in this way and be fixed there by closing the cover.

In one embodiment the cover is designed to cover the base along the whole outer contour and to extend preferably to the bottom of the base. This ensures that no contamination (food remnants) can enter into the inside of the bracket. Furthermore, the comfort in wear is considerably improved by a smooth, edge-free shape of the cover.

In accordance with a further aspect of the present invention, the invention comprises an orthodontic bracket kit. The kit includes at least one bracket having a cover integrally hinged to the base and a second, separate cover configured to attach to the base. The second cover does not have a shaped spring element, but rather locking elements for fastening the second cover to the base. In this embodiment, after the first integrally attached cover has been severed from the base, such as by use of a scalpel, the second cover can be put onto the base. Such a bracket kit allows the severing of the originally provided cover and the replacement of this cover with a separate cover. The second cover can be pressed onto the base in tight space conditions.

These and other objects and features of the present invention will become more fully apparent from the following description and appended claims, or may be learned by the practice of the invention as set forth hereinafter.

BRIEF DESCRIPTION OF THE DRAWINGS

The present invention is described below by means of example embodiments and with reference to the enclosed drawings, in which are shown.

DETAILED DESCRIPTION OF THE PREFERRED EMBODIMENTS

Figure 1:
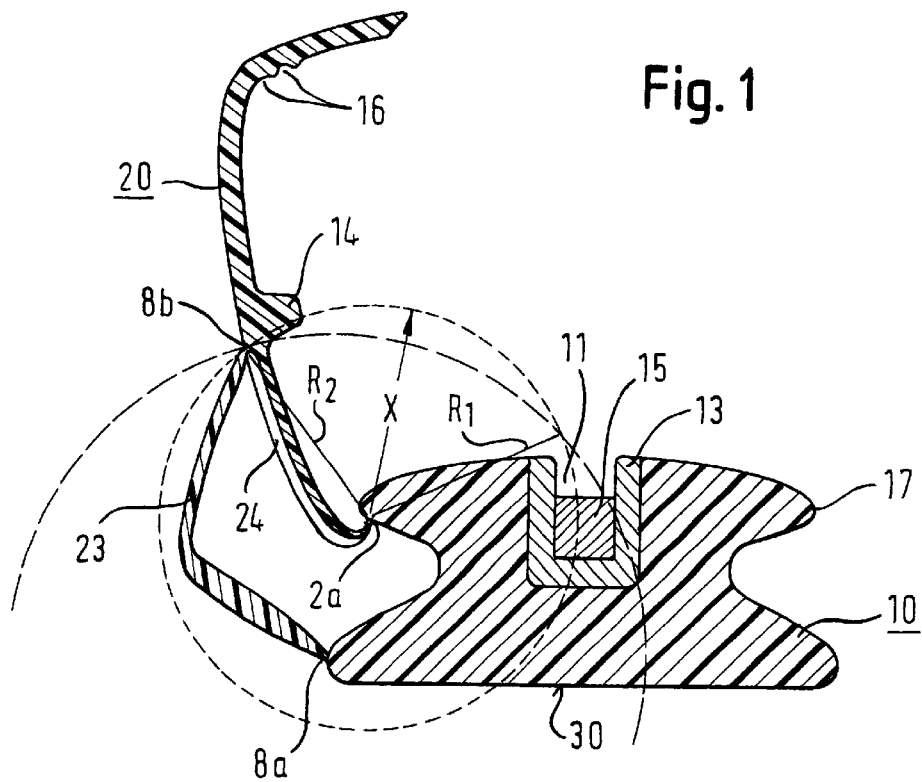
FIG. 1 is a cross sectional side view of an orthodontic bracket having an open cover.
Figure 2:
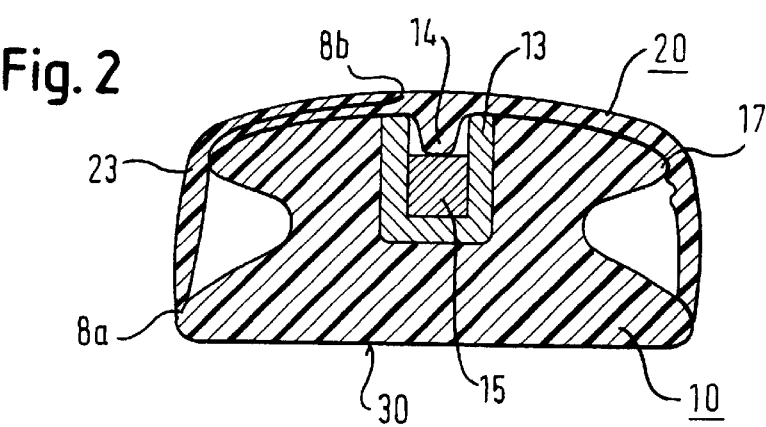
FIG. 2 is a cross sectional side view of the bracket shown in FIG. 1 with the cover closed.

The orthodontic bracket shown in FIGS. 1 and 2 is manufactured in one piece as an injection molded plastic part. The orthodontic bracket has an approximately anvil-like base 10 to which a cover 20 is hingedly connected. A slot 11 open to the upper side of the base 10 is provided at the center of said base 10 and serves for the insertion of an archwire 15. A reinforcement insert 13 is provided in the region of the slot 11. The reinforcement insert 13 is formed from a metal material and has a U-shape in cross-section. The basic material of the bracket is molded round the reinforcement insert 13 in the manufacturing process. The archwire 15 with a square cross-section is arranged inside the slot 11 and serves to correct the teeth in a known manner.

The cover 20 forms an approximately L-shaped hood in cross-section and is connected in one piece to the base 10 via an integral hinge 2a. Two exit apertures, which are not shown in FIGS. 1–4 and which are opposite to one another, are provided in each case in the cover 20. The cover 20 also has an insertion slot (cf. 32" and 34" in FIG. 5) for the passage of the archwire 15 following on from the lower edge of the cover.

A spring element 23 with an approximately L-shaped cross-section is hinged via a joint 8a in the region of the bottom 30 of the base 10. That is, the spring element 23 is attached via an integral hinge which is formed in the same way as the integral hinge 2a, i.e., by a corresponding reduction in the material cross-sections during injection molding. The spring element 23 is further hinged to the outside of the cover 20 via a further integral hinge 8b of the same design. The spring element 23 is connected roughly at the middle of the cover 20.

As is shown in particular in FIG. 2, the spring element 23 is completely integrated in the cover 20. As a result, the spring element 23 forms a hood-shaped, closed protective shell together with the cover 20 and said shell surrounds the complete outside contour of the base 10. A recess 24, open to the outside, but closed to the inside, is provided at the outside of the cover 20 for the integration of the spring 23 in the cover 20. The spring element 23 is completely received in the recess 24 in the closed state of the cover 20 so that the upper sides of the cover 20 and the spring element 23 form a uniform, continuous surface.

A plurality of locking recesses 16 are provided at the inside of the cover 20. The locking recesses 16 enable the cover 20 to be able to latch onto a closing nose 17 of the base 10.

Furthermore, a holding cam 14 is provided at the inside and middle of the cover 20 and fixes the archwire 15 in the slot 11 in the closed state (FIG. 2). The fixing is effected here only by closing the cover 20 and latching the locking recess 16 via the closing nose 17, i.e., the bracket is self-ligating.

As is illustrated in particular by FIG. 1, the integral hinge 8b, which serves as a joint, moves on a circular arc with a radius $R_1$ when the cover 20 is opened and closed. If the spring element 23 were not connected to the cover 20, the joint axis of the integral hinge 8b would move on a circular arc with a radius $R_2$ during rotation around the axis of the integral hinge 8a. However, due to hinge 8b being fixed at the cover 20, it necessarily moves on the circular arc with the radius $R_1$. The spring element 23 is elastically deformed in this way during the opening and closing process, with the maximum extension preferably being achieved in each case at approximately half the opening or closing angle. The spring force of the spring element 23 hereby supports the opening and closing of the cover 20 in the event of over- or underachievement of this angle in the one direction or the opposite one. When this angle is overachieved or underachieved, the spring element 23 is extended by the maximum path X.

Figure 3:
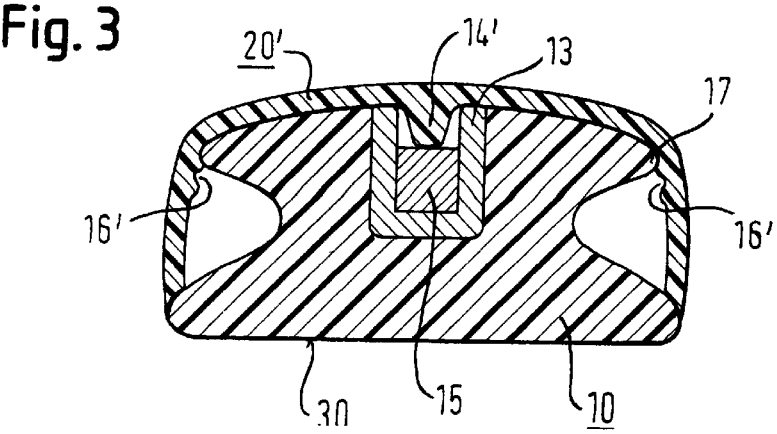
FIG. 3 is a cross sectional side view of the bracket shown in FIG. 1 with an alternative cover which is not connected to the base in one piece.

FIG. 3 shows a cross-section through a bracket in accordance with FIGS. 1 and 2, with, however, the cover 20 having been removed using a tool, for example a scalpel, by cutting through the integral hinges 2a and 8a. Such a measure can be necessary in particular when it is not or no longer possible for the cover 20 to flip open due to a certain tooth position. In this case, a second, separate cover 20' (FIG. 3) is provided. The cover 20' is formed approximately in a U-shape in cross-section and has a plurality of peripheral locking recesses 16' at its inside which can slide over the locking nose 17 of the base, whereby the cover 20' latches on the base 10. The cover 20' is accordingly essentially formed in a hood-like manner and has, like the cover 20, a holding cam 40 at its inside which holds the archwire 15.

Figure 4:
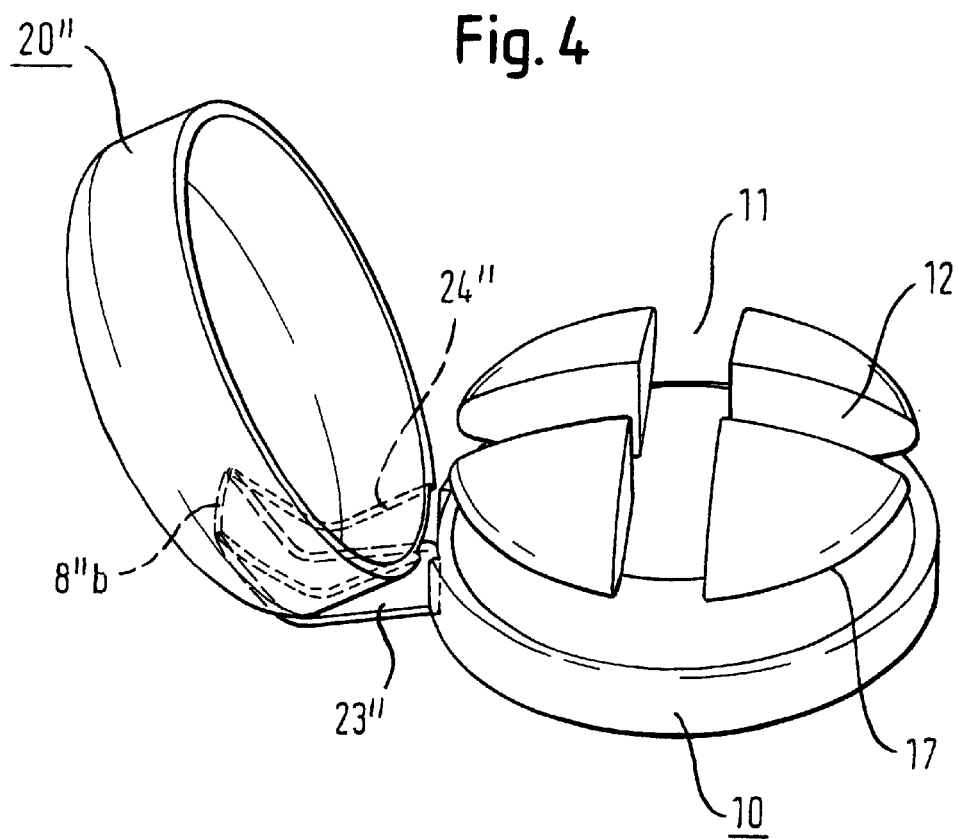
FIG. 4 is a perspective view of a further embodiment of a bracket having an open cover.
Figure 5:
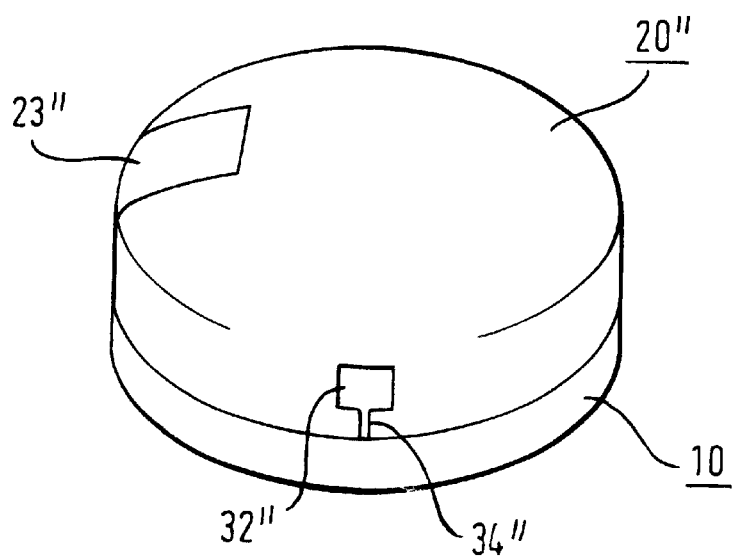
FIG. 5 is a perspective view of the bracket shown in FIG. 4 with the cover closed.

A further embodiment of a bracket in accordance with the invention is shown in FIGS. 4 and 5. The base 10 shown corresponds here to the base 10 of FIGS. 1 to 3. The base 10 in FIG. 4, however, includes a further slot 12 that is provided in addition to the slot 11 to receive the archwire 15. The further slot 12 extends transversely to the slot 11 and is capable of use in a known manner to help fix the archwire. The cover 20" is also formed in a hood-like manner and connected in one piece via an integral hinge 8"b to a joint element 23". The joint element 23" is formed in the same way as the spring element 23 of the embodiment in accordance with FIGS. 1 and 2. The element 23" does not, however, act as a spring element in the embodiment of FIGS. 4 and 5, but as a joint part. A recess 24", open to the outside, but closed to the inside, is, however, provided at the outside of the cover 20" in the same way as in the embodiment in accordance with FIGS. 1 and 2. The element 23" is completely received in said recess 24" in the closed state of the cover 20".

The end of the joint part 23" opposite the integral hinge 8"b is pushed into the groove of the base 10 in a form-locking manner, i.e., the joint part 23", and thus also the cover 20", are insertably fixed to the base 10. At the same time, a further integral hinge is provided in this region so that the joint part 23", and thus also the cover 20", can be pivoted such that the cover 20" can be placed onto the base 10.

Peripheral locking recesses (not shown) are in turn provided on the inside of the cover 20" and are formed in accordance with the locking projections 16' of FIG. 3. It is possible in this way to clip the cover 20" onto the base 10 after flipping over. FIG. 5 shows such a state in which the cover 20" is clipped onto the base 10. The exit aperture 32" already mentioned above can also be seen in this figure. An insertion slot 34" extending to the lower edge of the cover 20" and serving the passage of the archwire 15 follows on from said exit aperture 32". The cover 20" has two such insertion slots with connecting exit aperture, as do the covers 20 and 20'. These elements are, however, not shown in FIG. 4 for a more simplified representation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An orthodontic bracket comprising:
   a base having a slot adapted to receive an archwire;
   a cover hingedly formed on the base so as to selectively rotate between an open position and a closed position, the cover having a recessed region, the cover covering at least a portion of the slot when in the closed position, the cover and base being integrally formed together as a single piece; and
   a spring element extending between the cover and the base, at least a portion of the spring element being disposed within the recessed region of the cover when the cover is in the closed position.

2. An orthodontic bracket in accordance with claim 1, wherein the spring element extends to a maximum length when the cover is moved to or approximately midway between the open position and the closed position.

3. An orthodontic bracket in accordance with claim 1, wherein the cover and base are molded as a single piece from a single material, wherein the cover is secured to the base at an integral hinge region having a reduction in the material cross-section of the material.

4. An orthodontic bracket in accordance with claim 1, wherein the cover is secured to the base by an integral living hinge.

5. An orthodontic bracket in accordance with claim 1, wherein the spring element, the base, and the cover are integrally formed together as a single piece of a single material.

6. An orthodontic bracket in accordance with claim 5, wherein the spring element is secured to the base and the cover at integral hinge regions having a reduction in the material cross-section of the material.

7. An orthodontic bracket in accordance with claim 5, wherein the spring element has a first end and an opposing second end, the first end of the spring element being secured to the cover by an integral living hinge, the second end of the spring element being secured to the base by an integral living hinge.

8. An orthodontic bracket in accordance with claim 1, further comprising at least one locking recess or closing nose which is provided on the cover or the base.

9. An orthodontic bracket in accordance with claim 1, wherein the cover has a recess open to the outside, but closed to the inside, in which the spring element or a hinge part is substantially received when the cover is moved to the closed position.

10. An orthodontic bracket in accordance with claim 1, wherein the base has an outer contour and a bottom, the cover covering the base along the whole outer contour and substantially extending to the bottom.

11. An orthodontic bracket in accordance with claim 1, further comprising a holding cam projecting from the cover such that the holding cam is received within the slot of the base when the cover is moved into the closed position.

12. An orthodontic bracket in accordance with claim 1, wherein the spring element, the base, and the cover are integrally formed from plastic.

13. An orthodontic bracket in accordance with claim 12, further comprising a reinforcement insert secured within the slot of the base, the reinforcement insert being comprised of a metal and having a substantially U-shaped transverse cross section.

14. An orthodontic bracket kit comprising:
   at least one orthodontic bracket comprising:
      a base having a slot adapted to receive an archwire; and
      a first cover hingedly formed on the base so as to selectively rotate between an open position and a closed position, the cover covering at least a portion of the slot when in the closed position, the first cover being initially secured to the base by an integral hinge of reduced cross-section that can be severed so as to selectively separate the first cover from the base; and
      a second cover separate from the first cover and not initially attached to the base, the second cover having at least one locking element and being configured for attachment of the second cover to the base after separation of the first cover from the base.

15. An orthodontic bracket comprising:
   a base having a slot adapted to receive an archwire;
   a cover having a first end integrally secured to the base by a living hinge, the cover being selectively rotated between an open position and a closed position, the cover covering at least a portion of the slot when in the closed position; and
   a spring element having a first end and an opposing second end, the first end of the spring element being integrally secured to the cover by a living hinge, the second end of the spring element being integrally secured to the base by a living hinge; the base, cover, and spring element being integrally formed from plastic.

16. An orthodontic bracket in accordance with claim 15, wherein the spring element extends to a maximum length when the cover is moved midway between the open position and the closed position.

17. An orthodontic bracket in accordance with claim 16, further comprising the cover having a recessed region, at least a portion of the spring element being disposed within the recessed region of the cover when the cover is moved into the closed position.

18. An orthodontic bracket in accordance with claim 17, further comprising a reinforcement insert secured within the slot of the base, the reinforcement insert being comprised of a metal and having a substantially U-shaped transverse cross section.

19. A one-piece, injection molded plastic orthodontic bracket comprising:
   a base having a slot adapted to receive an archwire;
   a cover hingedly attached to the base so as to selectively rotate between an open position and a closed position, the cover covering at least a portion of the slot when in the closed position; and a hinge element interposed between the base and cover comprising a region having a reduction in material cross-section compared to material cross-sections of the base and cover immediately adjacent to the hinge element; so as to form an integral living hinge that attaches the cover to the base, and that is not biased toward the closed position, and the cover, base and hinge element together being injection molded so that they comprise a one-piece plastic orthodontic bracket.

20. An orthodontic bracket in accordance with claim 19, further including a spring element that selectively biases the cover so as to remain in the closed position when in the closed position and so as to remain in the open position when in the open position.

21. An orthodontic bracket comprising:

a base having a slot adapted to receive an archwire;

a cover hingedly attached to the base by a hinge so as to selectively rotate about the hinge between an open position and a closed position, the cover covering at least a portion of the slot when in the closed position; and a spring element extending between the cover and the base, wherein the spring element selectively biases the cover so as to remain in the closed position when in the closed position and so as to remain in the open position when in the open position, the spring element, base and cover being integrally molded together as a single piece of plastic such that no separate assembly is required in order to attach the spring element, base and cover together.

22. An orthodontic bracket comprising:

a base having a slot adapted to receive an archwire;

a cover hingedly attached to the base by a hinge so as to selectively rotate about the hinge between an open position and a closed position, the cover covering at least a portion of the slot when in the closed position; and a spring element cooperating with the cover and the base in a manner so that when the cover is in the open position the spring element biases the cover toward the open position, the base, cover and spring element being integrally formed together as a single piece.

23. An orthodontic bracket as defined in claim 22, the spring element also biasing the cover toward the closed position when the cover is in the closed position.

24. An orthodontic bracket as defined in claim 22, the spring element, base and cover being molded as a single piece of plastic such that no separate assembly is required in order to attach the spring element, base and cover together.

* * * * *